United States Patent [19]

Holland et al.

[11] 4,228,107

[45] Oct. 14, 1980

[54] POLYHALOGENATED HYDROCARBONS, USEFUL AS INSECTICIDE INTERMEDIATES, AND METHODS FOR THEIR PREPARATION

[75] Inventors: David Holland, Runcorn; David J. Milner, Manchester; Roger K. Huff, Walesby, Nr. Newark, all of England

[73] Assignee: Imperial Chemical Industries Limited, London, England

[21] Appl. No.: 40,047

[22] Filed: May 17, 1979

[30] Foreign Application Priority Data

May 25, 1978 [GB] United Kingdom ............... 22430/78

[51] Int. Cl.$^2$ ............................................. C07C 19/08
[52] U.S. Cl. ..................................... 570/134; 570/137
[58] Field of Search .......................................... 260/653

[56] References Cited

U.S. PATENT DOCUMENTS 3,310,589   3/1967   Ketley ................................. 260/653

OTHER PUBLICATIONS

Burton et al., Tetrahedron Letters, No. 42, pp. 5163–5168, 1966.

*Primary Examiner*—C. Davis
*Attorney, Agent, or Firm*—Cushman, Darby & Cushman

[57] ABSTRACT

Polyhalogenated hydrocarbons of general formula RR$^1$CH—CHX—CH$_2$CYZQ wherein R is hydrogen or lower alkyl, R$^1$ is lower alkyl, X is Cl, Br or I, Y is F, Cl or Br, Z is Y or Q and Q is a group W(CF$_2$)$_m$—in which W is hydrogen, F or Cl and m is 1 or 2, provided that X is always Br or I when at least one of Y and Z is Br, and a process for preparing these polyhalogenated hydrocarbons by reacting an alkyl-substituted butene with a polyhalogenated alkane having from 2 to 4 carbon atoms, in the presence of a catalyst.

3 Claims, No Drawings

POLYHALOGENATED HYDROCARBONS, USEFUL AS INSECTICIDE INTERMEDIATES, AND METHODS FOR THEIR PREPARATION

This invention relates to novel halogenated hydrocarbons, useful as insecticide intermediates, and to methods for their preparation.

According to the present invention, we provide, as new compounds, polyhalogenated hydrocarbons of general formula:

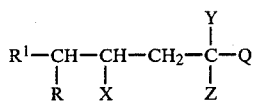

wherein
R is hydrogen or a lower alkyl group,
$R_1$ is lower alkyl,
X is chloro, bromo or iodo,
Y is fluoro, chloro or bromo,
Z is Y or Q, and
Q is a group of formula $W(CF_2)_m-$,
where W is hydrogen, fluoro or chloro and m is 1 or 2, provided that X is always bromo or iodo when at least one of Y and Z is bromo.

Preferably X is chloro or bromo, especially a chloro. By "lower alkyl" we mean an alkyl group having from 1 to 6 carbon atoms, especially methyl.

The compounds of the invention may be prepared by suitable classical processes of organic chemistry. However, especially useful processes comprise reacting an alkyl substituted butene with a polyhalogenated alkane having from 2 to 4 carbon atoms, in the presence of a suitable catalyst, for example as described by Burton, et al, in Tetrahedron Letters No 42, pp 5163–5168, 1966, Permagon Press Limited. The reaction is best carried out in the presence of an amine, for example ethanolamine or diethylamine, using a metal halide as catalyst. Copper and iron halides are especially useful as catalysts.

Typically the polyhalogenated alkane and alkyl-substituted butene are mixed with the amine and metal halide catalyst in alcohol and heated for 20–30 hours at a temperature in the range 50° to 200° C. with constant stirring. The desired product may then be recovered by distillation, first at atmospheric pressure to remove the solvent and then under reduced pressure to distill off the product. Yields of 60–80% (calculated on the alkyl-substituted butene) may be readily obtained. Examples of polyhalogenated alkanes which may be reacted with 3-methylbut-1-ene to give especially useful products are set out in the Table below.

TABLE

| Polyhalogenated Alkane | Polyhalogenated Hydrocarbon Product |
|---|---|
| Br–C(Br)(Br)–CF$_3$ | CH$_3$–CH(CH$_3$)–CH(Br)–CH$_2$–C(Br)(CF$_3$)–CF$_3$ |
| Cl–C(Cl)(Cl)–CF$_3$ | CH$_3$–CH(CH$_3$)–CH(Cl)–CH$_2$–C(Cl)(CF$_3$)–CF$_3$ |
| Br–C(Br)(CF$_3$)–CF$_3$ | CH$_3$–CH(CH$_3$)–CH(Br)–CH$_2$–C(Br)(CF$_3$)–CF$_3$ |
| Cl–C(Cl)(CF$_3$)–CF$_3$ | CH$_3$–CH(CH$_3$)–CH(Cl)–CH$_2$–C(Cl)(CF$_3$)–CF$_3$ |
| Cl–C(Cl)(Cl)–(CF$_2$)$_2$Cl | CH$_3$–CH(CH$_3$)–CH(Cl)–CH$_2$–C(Cl)(Cl)–(CF$_2$)$_2$Cl |

The compounds according to our invention, especially those referred to in the Table above, in which the halogen is chlorine or bromine, and group R is methyl, may be converted into halogenated dienes which are useful as intermediates in the preparation of insecticides. An especially convenient process for effecting this conversion is described in detail in our co-pending patent application of even date.

The invention will be illustrated by the following Examples.

EXAMPLE 1

A mixture containing trifluorotrichloroethane (37.5 g) 3-methylbut-1-ene (7.0 g), copper (I) chloride (0.1 g) ethanolamine (3.05 g) in tertiary butyl alcohol (100 ml) was placed in a glass-lined stainless steel autoclave. The mixture was maintained at 80° C. for approximately 29 hours, with constant stirring.

The resulting brown solution was distilled at atmospheric pressure to remove the alcohol and the remaining solution was distilled under reduced pressure (0.5–0.6 mm Hg) and the fraction boiling at 40° C. collected. The yield of product was 20.6 g (80%)

The structure of the product, i.e.

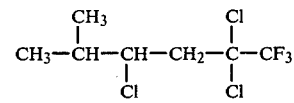

was confirmed by NMR spectroscopy and mass spectrographic analysis.

| | | C | H | Cl | F |
|---|---|---|---|---|---|
| Analysis | % Required | 32.62 | 3.88 | 41.36 | 22.14 |
| | % Found | 32.35 | 3.80 | 39.80 | 21.80 |

EXAMPLE 2

A mixture containing trifluorotrichloroethane (50 g) 3-methylbut-1-ene (6.2 g), ferrous chloride tetrahydrate (0.355 g) and diethylamine hydrochloride (0.29 g) in methanol (5.7 g) was placed in a glass-lined stainless steel autoclave. The mixture was maintained at 130° C. for approximately 29 hours with constant stirring.

The product, which was shown by analysis to be the same as in Example 1, was recovered by the same procedure. The yield of product was 60%.

We claim:

1. Polyhalogenated hydrocarbons of general formula:

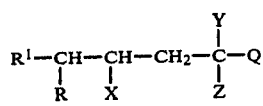

wherein

R is hydrogen or a lower alkyl group,
$R^1$ is lower alkyl,
X is chloro, bromo or iodo,
Y is fluoro, chloro or bromo,
Z is Y or Q, and
Q is a group of formula $W(CF_2)_m-$
wherein W is hydrogen, fluoro or chloro and m is 1 or 2, provided that X is always bromo or iodo when at least one of Y and Z is bromo.

2. Polyhalogenated hydrocarbons as claimed in claim 1 wherein X is chloro or bromo.

3. 5-Methyl-2,2,4-trichloro-1,1,1-trifluorohexane.